United States Patent
Bauerfeind et al.

(10) Patent No.: US 8,235,927 B2
(45) Date of Patent: Aug. 7, 2012

(54) WRIST ORTHOSIS

(76) Inventors: Hans B. Bauerfeind, Zeulenroda (DE); Holger Reinhardt, Kempen (DE)

( * ) Notice: Subject to any disclaimer, the term of this patent is extended or adjusted under 35 U.S.C. 154(b) by 479 days.

(21) Appl. No.: 12/439,942

(22) PCT Filed: Aug. 28, 2007

(86) PCT No.: PCT/EP2007/007532
§ 371 (c)(1),
(2), (4) Date: Nov. 6, 2009

(87) PCT Pub. No.: WO2008/028588
PCT Pub. Date: Mar. 13, 2008

(65) Prior Publication Data
US 2010/0113997 A1    May 6, 2010

(30) Foreign Application Priority Data
Sep. 4, 2006 (DE) .......................... 10 2006 041 441

(51) Int. Cl.
*A61F 5/00* (2006.01)
(52) U.S. Cl. ........................................... 602/21; 602/20
(58) Field of Classification Search .......... 602/5, 20–21, 602/60–61, 64; 2/16; D24/190–192; 128/878–879
See application file for complete search history.

(56) References Cited

U.S. PATENT DOCUMENTS

| 4,873,968 | A | * | 10/1989 | Finnieston et al. | 602/21 |
|---|---|---|---|---|---|
| 5,193,771 | A | * | 3/1993 | Hassel et al. | 248/118 |
| 5,725,490 | A | * | 3/1998 | Conran | 602/21 |
| 5,759,166 | A | | 6/1998 | Nelson et al. | |
| 6,254,051 | B1 | * | 7/2001 | Hubbard et al. | 248/313 |
| 6,322,462 | B1 | * | 11/2001 | Kafer | 473/458 |
| 6,629,760 | B1 | * | 10/2003 | Razin | 351/156 |
| 7,824,352 | B2 | * | 11/2010 | Jaccard | 602/20 |
| 7,867,182 | B2 | * | 1/2011 | Iglesias et al. | 602/20 |
| 2004/0049141 | A1 | | 3/2004 | Slautterback et al. | |

FOREIGN PATENT DOCUMENTS

| DE | 88 06 792 U1 | 8/1988 |
|---|---|---|
| EP | 1 382 316 A1 | 1/2004 |
| WO | WO-02/17827 A1 | 3/2002 |

* cited by examiner

*Primary Examiner* — Patricia Bianco
*Assistant Examiner* — Camtu Nguyen
(74) *Attorney, Agent, or Firm* — Birch, Stewart, Kolasch & Birch, LLP

(57) ABSTRACT

The invention relates to a wrist orthosis with a cuff, which is open for passage of the thumb and which is provided with stabilizing rods and with at least one tightening strap for fixing the orthosis on the wrist. The cuff has two adjacent thumb openings for receiving either the left or right thumb, wherein a central stabilizing rod extends between the thumb openings, and a lateral stabilizing rod extends along the outer side of each said opening in such a manner that the thumb openings are each located between the central stabilizing rod and the relevant lateral stabilizing rod.

8 Claims, 5 Drawing Sheets

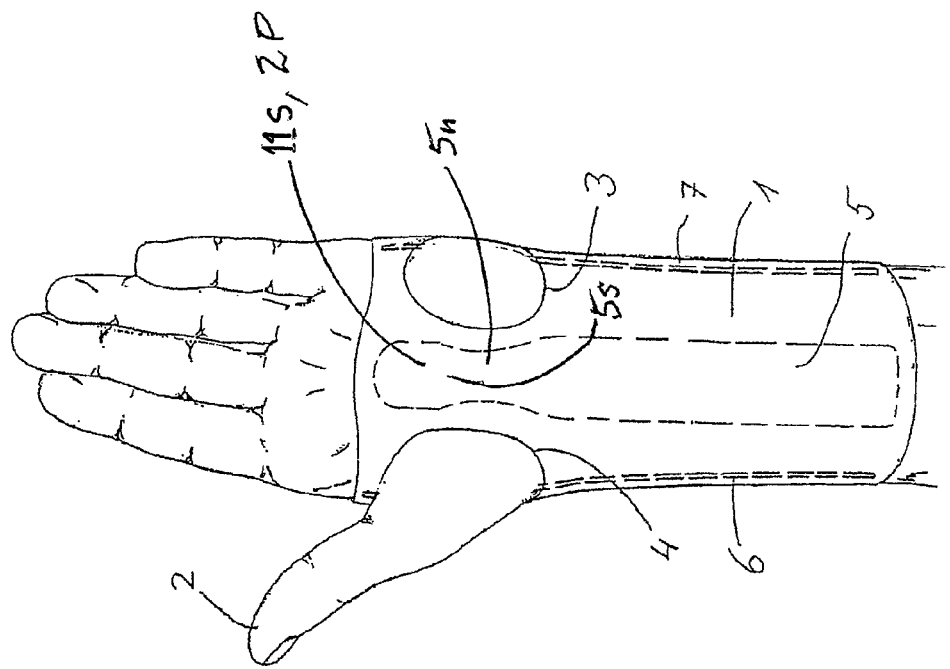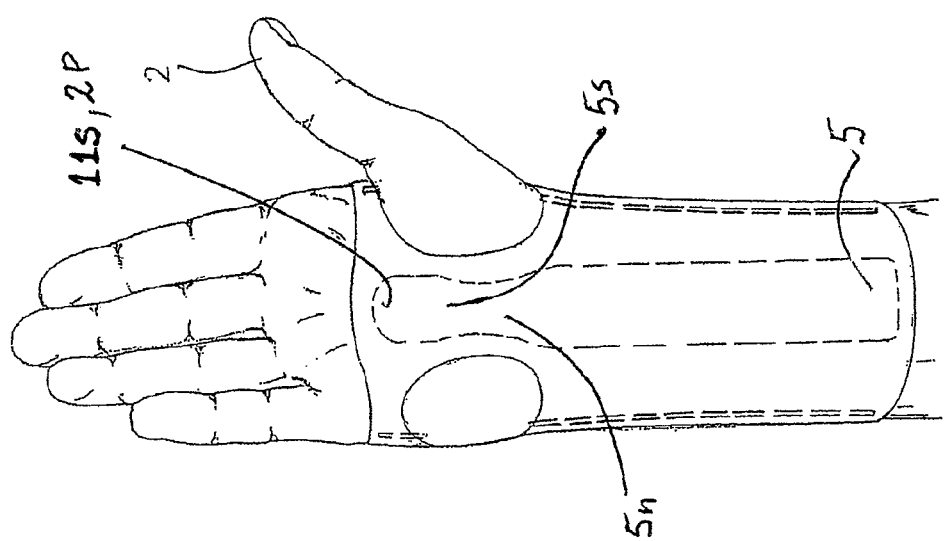

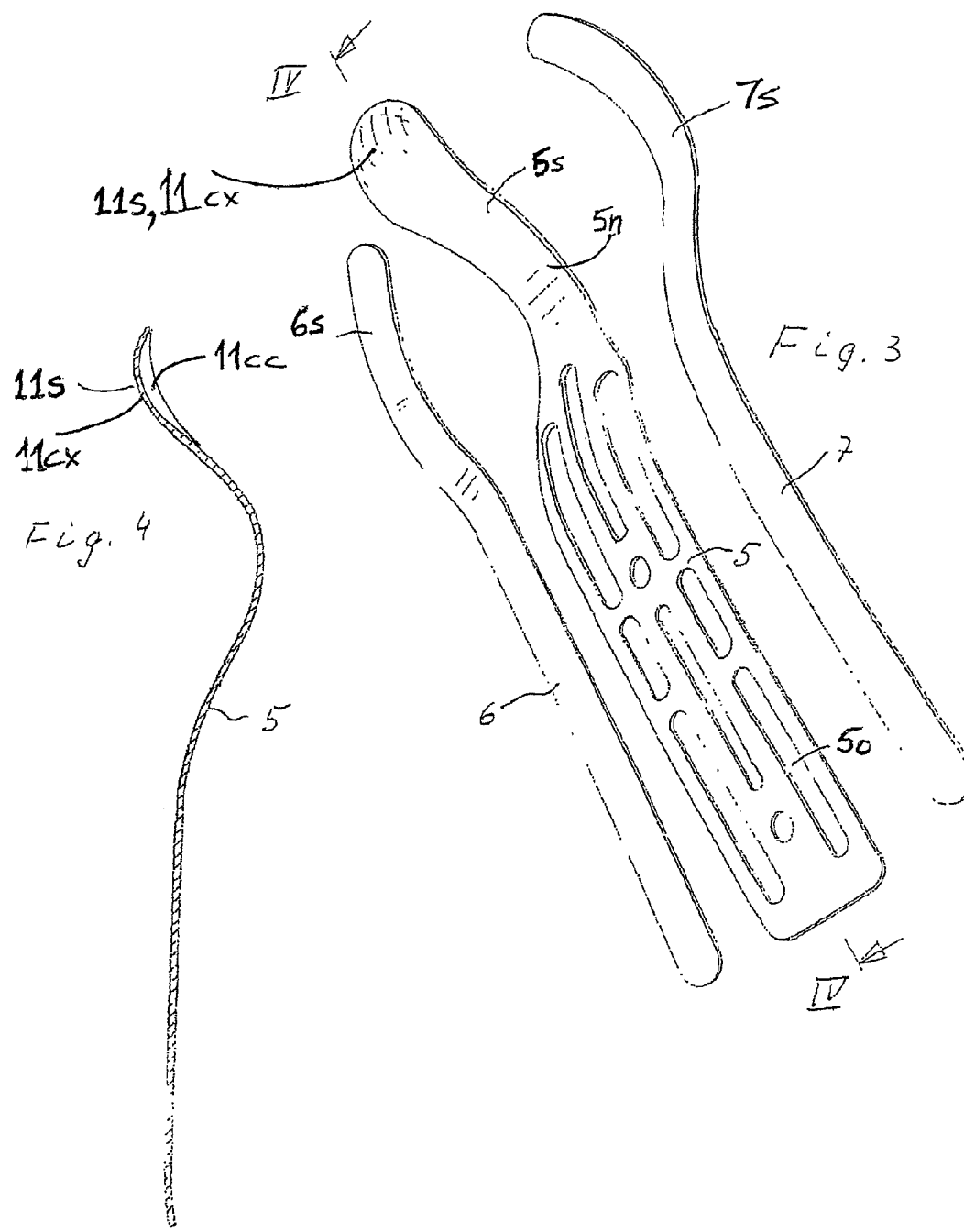

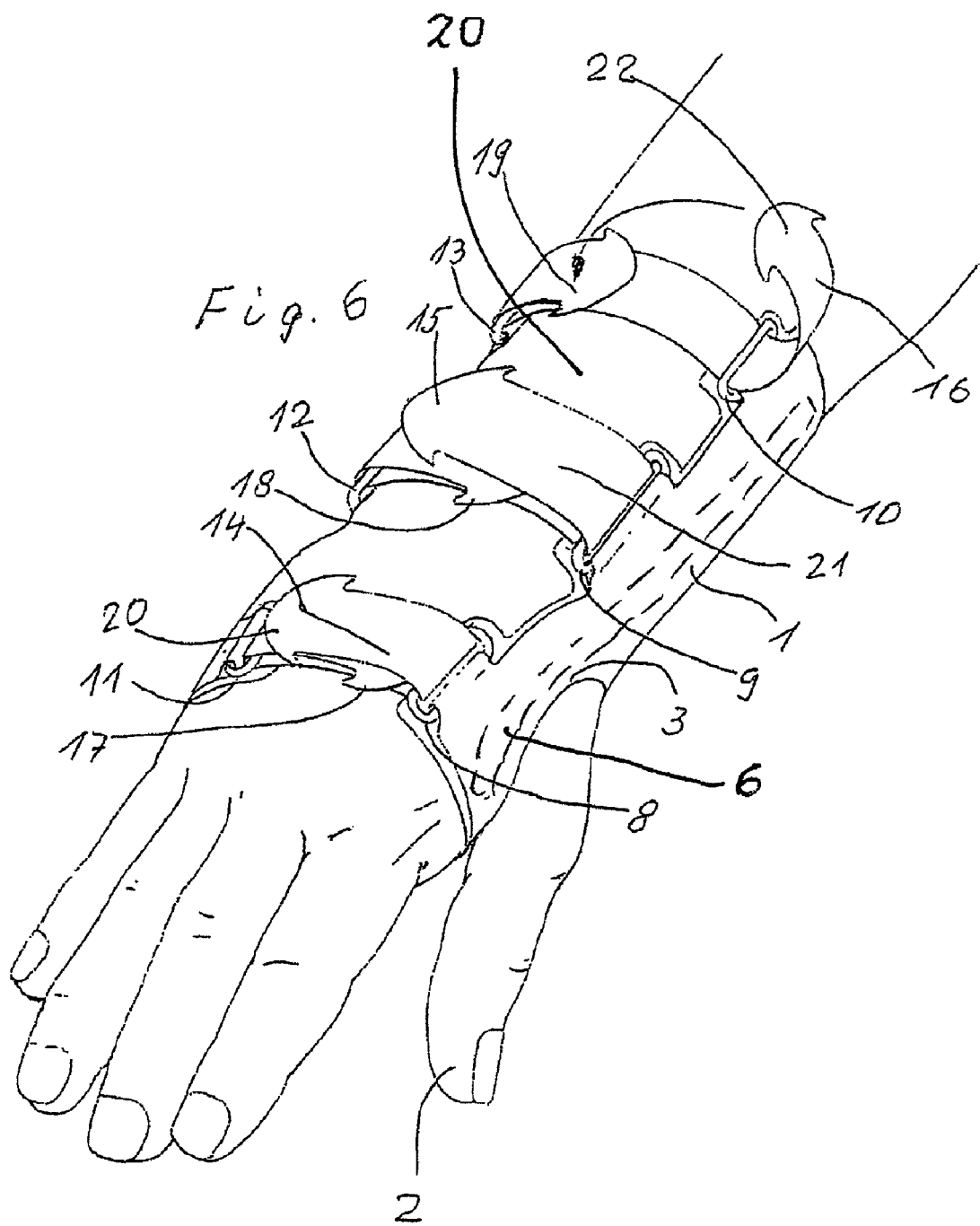

WRIST ORTHOSIS

CROSS-REFERENCE TO RELATED APPLICATION

Figure 1:
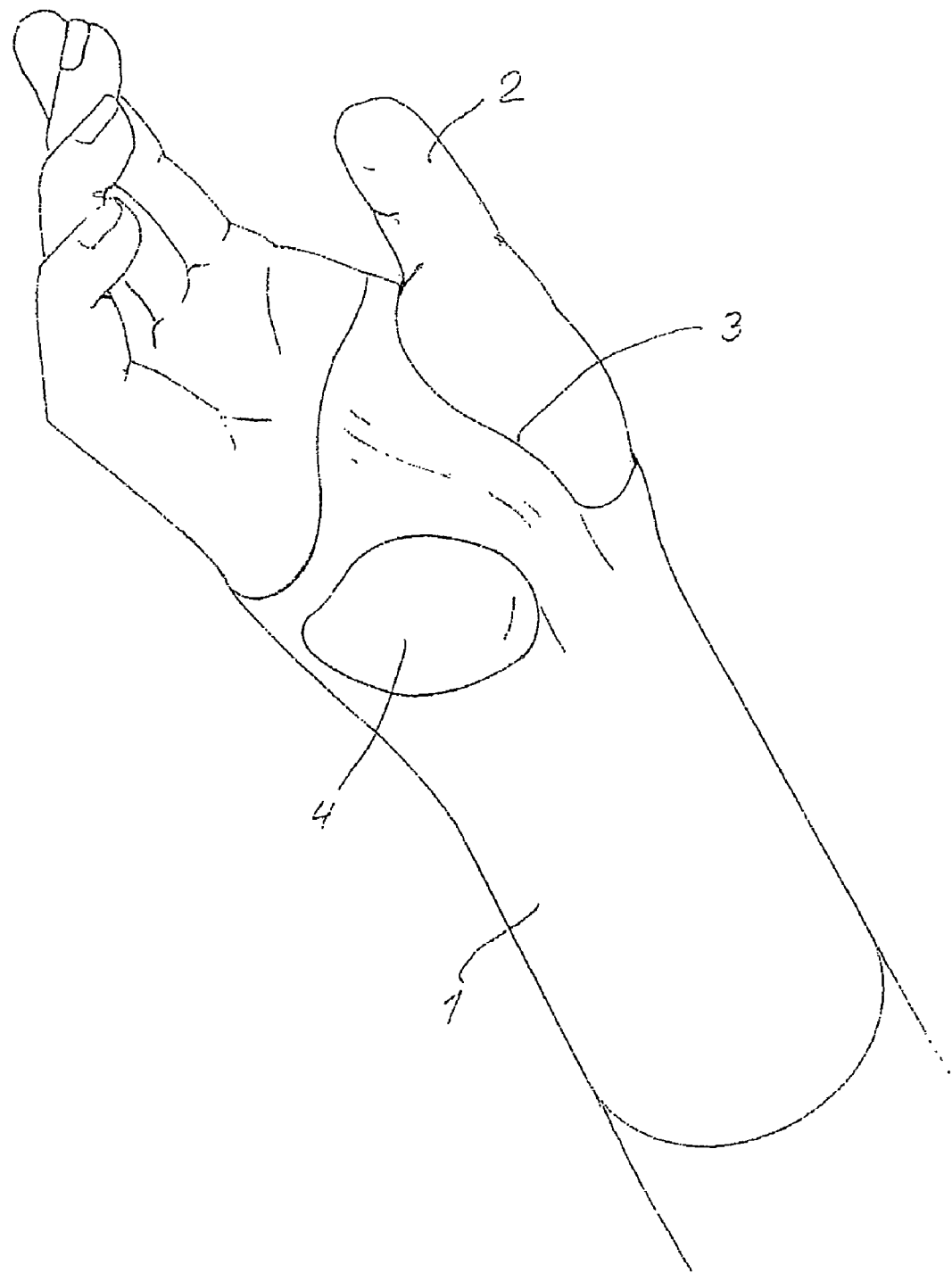

The present application claims priority under 35 U.S.C. §119 to PCT/EP Application 2007/007532 filed Aug. 28, 2007 and German Patent Application No. 10 2006 041 441.1 filed Sep. 4, 2006.

The invention relates to a wrist orthosis with a cuff, which is open for passage of the thumb and which is provided with stabilizing rods and with at least one tightening strap for fixing the orthosis on the wrist, and which also has two adjacent thumb openings for receiving either the left or right thumb, wherein a central stabilizing rod extends between the thumb openings and a lateral stabilizing rod extends along the outer side of each said opening.

A similar orthosis is disclosed in the PCT document WO 02/17827 A1. This prior art wrist orthosis is made specifically for either a right or left hand in each case, for which purpose a corresponding opening is provided in the cuff of the orthosis for, e.g., the left thumb. The tightening straps used in this wrist orthosis are bent back at their ends in the manner of a hook in order to prevent the tightening straps from unintentionally pulling out of rings secured to the cuff. Since this design of orthosis is always configured either for the left or for the right hand in each case, as mentioned, and the orthosis thus cannot be transferred from the right hand to the left or vice versa, there was always a need to have a wrist orthosis available that is directly suitable for both the left and right wrists. In order to at least partially fulfill this object, the wrist orthosis evident from the European patent application EP 1 382 316 A1 was created, in which a relatively large opening for the thumb is provided in the cuff that makes it possible to slip the orthosis over the hand and the wrist in either one lengthwise direction or the opposite lengthwise direction, with the orthosis being capable of accommodating the left and the right hand in alternation, this being made possible by the fact that the opening for the thumb is made large enough that the orthosis can be drawn onto either the right or left hand. However, this usability for both the left and right hands presupposes that, in addition to the appropriately large thumb opening in the orthosis, receptacles are provided for stabilizing rods, and when the orthosis is being switched from, e.g., the left to the right hand, the stabilizing rods have to be inserted in opposite directions in pockets provided for this purpose. Hence, this means that the orthosis cannot be used directly for either the left or the right hand, which is to say it has to be reconfigured accordingly in each case.

The object of the invention is to create a wrist orthosis that can be used for the right or left hand without reconfiguration. For this purpose, the orthosis explained above is configured according to the invention such that the thumb openings are each located between the central stabilizing rod and the relevant lateral stabilizing rod, and the stabilizing rods are designed with a three-dimensional curvature in the region where they extend adjacent and conforming to the thumb openings.

As a result of the arrangement of two separate thumb openings located adjacent to one another in the cuff of the orthosis, it is possible to introduce either the left or the right hand into said orthosis from the same side without difficulty, with the thumb entering either one thumb opening or the other in each case. It is not necessary to exchange or make any changes to the stabilizing rods, since they are designed such that they work together equally well in the vicinity of either thumb opening, so that if the wrist orthosis is initially used for the left hand, it can later be placed directly on the right hand without making any changes. The stabilizing rods that come into action in this regard are arranged in the cuff such that they extend in the same manner to both thumb openings, so that the orthosis is suitable for use on either a left or right hand without further ado. This is thus accomplished by the means that the extent of the stabilizing rods is designed in a special manner such that a central stabilizing rod extends between the thumb openings, and a lateral stabilizing rod is provided at each thumb opening opposite the central stabilizing rod, hence three stabilizing rods in all, so that each thumb opening is located between the central stabilizing rod and a lateral stabilizing rod. In this way, the wrist orthosis can be drawn directly onto either the left or the right hand without any modifications to it. In order to prevent the stabilizing rods from exerting bothersome pressure on any part of the hand, in particular the thumb, when the wrist orthosis is being worn, the stabilizing rods are usefully designed with a three-dimensional curvature in the region where they extend adjacent and conforming to the thumb openings, by which means the stabilizing rods more or less encompass the thumb passing through the applicable thumb opening.

In aid of a symmetrical design of the wrist orthosis and its tightening straps, they are advantageously designed such that the tightening straps are passed through rings located at the outer edge of the cuff, and can be placed on and adhered to themselves by means of hook-and-loop fasteners with one end on the applicable tightening strap between the rings and the other end on the back of this tightening strap, which is to say on the ends of the tightening straps that are looped around the rings. This accomplishes the result that the ends of the tightening straps are raised only slightly from the cuff, and thus do not undesirably make themselves noticeable when a wrist orthosis is worn.

It is also possible to secure the tightening straps to the rings in terms of their position, which is accomplished by the means that the ends of the tightening straps are widened with respect to the rings such that the widenings act as barbs to prevent unintentional passage through the rings. As compared to loops at the ends of the tightening straps, such as are described in the aforementioned document WO 02/17827 A1, this design has the advantage that it essentially does not extend beyond the circumference of the applied wrist orthosis at all, since the widenings act like a barb. The tightening straps can still be threaded into the rings without difficulty, however, since they are made of textile material in the customary manner and can easily be compressed laterally in order to pass them through the rings.

Figure 5:
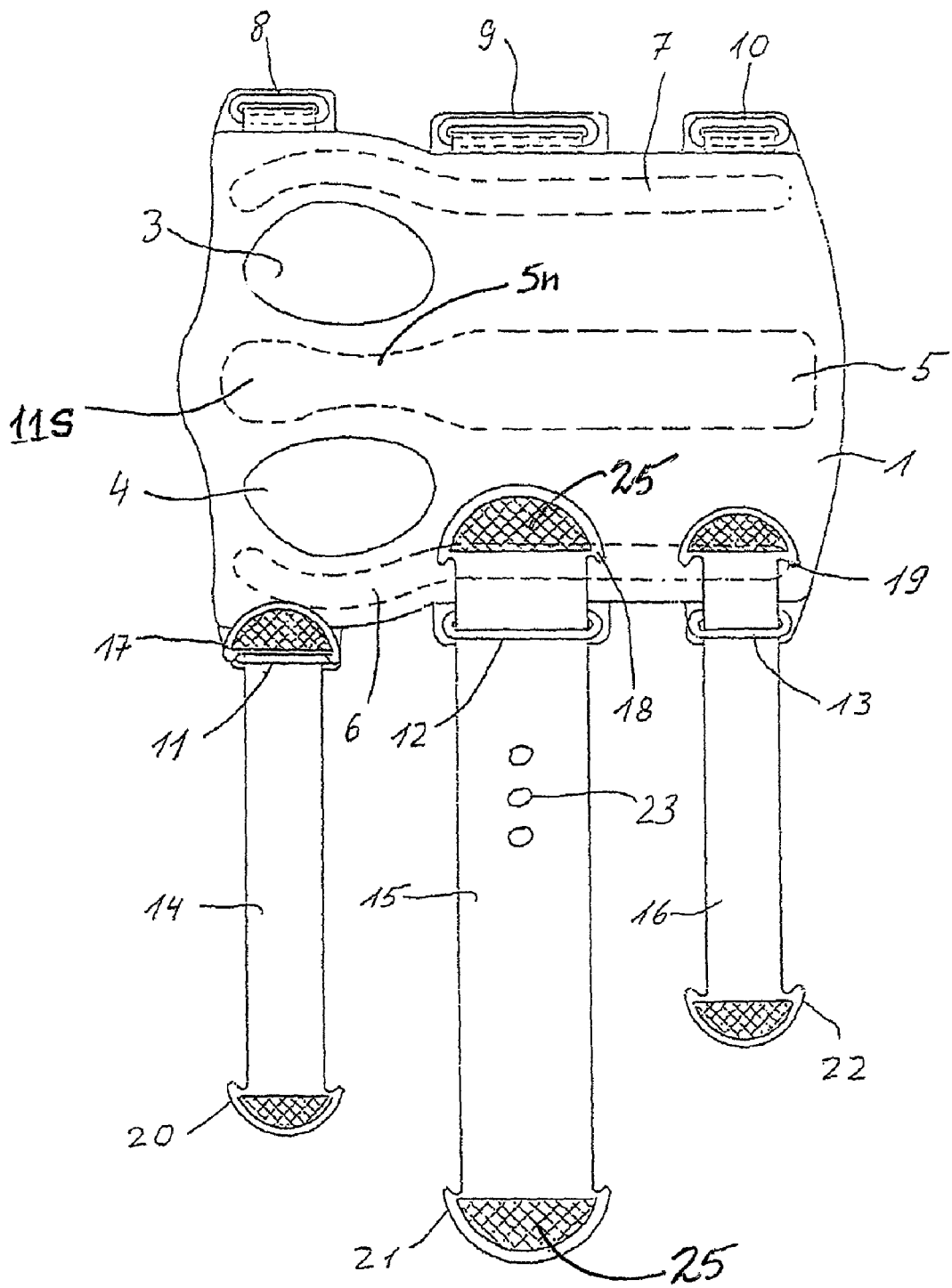

So that the wrist orthosis cannot cause heat buildup on the wrist in question, the cuff, the stabilizing rods, and the tightening straps are provided with openings which ensure that air can continuously reach the applicable parts of a hand. The figures depict example embodiments of the invention. Shown are:

FIG. 1 a right wrist with a view of the palm and with the wrist orthosis in place;

FIGS. 2a and 2b a right hand and a left hand, each with a wrist orthosis in place, with the stabilizing rods represented;

FIG. 3 the three stabilizing rods from a wrist orthosis, shown separately;

FIG. 4 a stabilizing rod that runs on the outside next to the thumb, shown by itself;

FIG. 5 the wrist orthosis removed from the wrist;

FIG. 6 the wrist orthosis in place on a right hand, with a view of the tightening straps.

FIG. 1 shows a right hand with the wrist orthosis 1 with a cuff-shaped part 1c, in which the thumb 2 has passed through a thumb opening 3, and the other thumb opening 4 is unoccupied.

If this wrist orthosis 1 were to be placed on a left hand, then the left thumb would pass through the thumb opening 4.

FIGS. 2a and 2b show a right hand and a left hand, each of them wearing the same wrist orthosis 1, wherein the thumb 2 in FIG. 2a passes through the thumb opening 3, and the thumb opening 4 is unoccupied.

In FIG. 2b, a left hand is provided with the wrist orthosis 1, with the thumb 2 passing through the thumb opening 4, while the thumb opening 3 is left empty.

FIGS. 2a and 2b also show the stabilizing rods 5, 6, and 7 in dashed lines, since they are accommodated in corresponding pockets in the fabric of the wrist orthosis 1, and thus are not directly visible from outside. It is evident from the position in which the stabilizing rods 5, 6, and 7 are shown that the stabilizing rod 5 extends between the thumb openings 3 and 4 as the central stabilizing rod, while the lateral stabilizing rods 6 and 7 each extend along the outside of the wrist orthosis 1 such that each thumb opening 3 and 4 is laterally encompassed by two stabilizing rods, namely the thumb opening 3 by the stabilizing rods 5 and 7, and the thumb opening 4 by the stabilizing rods 5 and 6. This ensures that, in the region of each of the two thumb opening 3 and 4, two of the stabilizing rods 5, 6, and 7 are on opposite sides of the thumb 2 extending through either of thumb opening 3 or thumb opening 4, namely either the stabilizing rods 5 and 7 or the stabilizing rods 5 and 6. Complete symmetry prevails within the wrist orthosis 1, which can therefore easily be drawn equally well onto either the right hand (see FIG. 2a) or the left hand (see FIG. 2b) without the need to make any change to the wrist orthosis 1.

So that no pressure is exerted on the thumb extending through either of the thumb openings 3, 4 by the stabilizing rods 5, 6, 7, they are designed to curve where they extend adjacent to the thumb openings such that they three-dimensionally encompass the thumb. To this end, reference is made to the region 6s with regard to the stabilizing rod 6, and to the region 7s with regard to the stabilizing rod 7, which show when compared that the regions 6s and 7s have a three-dimensional curvature, and thus more or less encompass the thumb, but are curved in their transverse direction such that the thumb 2 is more or less enclosed laterally by them. The same applies to the stabilizing rod 5, which likewise has curvatures in both the longitudinal and transverse directions in the relevant region 5s.

The design of the stabilizing rod 5 is also shown in FIG. 4 as a cross-section along the line IV-IV from FIG. 3, from which it is evident that stabilizing rod 5 has a narrow region 5n between the thumb holes 3 and 4, and a relatively long rounding in region 5s which also forms a sort of spoon 11S near the end of region 5s, which likewise indicates a three-dimensional curvature. As can be seen in FIGS. 3 and 4, the spoon 11S near the end of region 5s has a convex-shaped upper side 11cx and concave-shaped lower side 11cc which faces away from a palm 2P of a left or right hand of the person wearing the orthosis.

FIG. 5 shows the wrist orthosis 1 after removal, with a direction of view toward the part of the orthosis that extends over the back of the hand. The view in FIG. 5 shows the orthosis 1 in a flat, extended position, with the two thumb openings 3 and 4, as well as the central stabilizing rod 5 and the lateral stabilizing rods 6 and 7. Attached to one side of the orthosis are the rings 8, 9, and 10, opposite which are the rings 11, 12, and 13 on the opposing side of the orthosis. The tightening straps 14, 15, and 16, which are provided at their two ends with the widenings 17, 18, 19 and 20, 21, and 22, are drawn through the rings 11, 12, and 13. These widenings can be elastically compressed, since the tightening straps 14, 15, and 16 are made in a known manner from a suitably compressible textile material. As a result of the use of these widenings, they each act as barbs, so that they cannot be pulled out of the relevant rings when the tightening straps 14, 15, and 16 are pulled. Nonetheless, they can be forced through the rings beforehand without difficulty on account of their flexibility. To avoid heat buildup on the hand caused by the wearing of the wrist orthosis, the cuff-shaped part 1c of the orthosis 1 as well as the tightening straps and the stabilizing rods are provided with openings; the tightening strap 15 in FIG. 5 is shown with several of these openings 23, which extend in like manner over the other aforementioned components of the orthosis (for example, see FIG. 3, which illustrates openings 5o in central stabilizing rod 5).

FIG. 6 shows a wrist orthosis 1 placed on a right hand, with the thumb 2 passing through the thumb opening 3, and also shows the tightening straps 14, 15, and 16, of which the tightening strap 16 is shown in a position prior to attachment to the widening 19. The arrow pointing away from the widening 22 indicates that, after the tightening strap 16 is tightened, the widening 22 can be brought to the back of the opposite side of the tightening strap 16 in the vicinity of the widening 19, where the widening 22 can then be attached by its hook-and-loop fastener 25 to a matching hook-and-loop fastener 25 in the vicinity of the widening 19. The same applies to the tightening and placement of the tightening straps 14 and 15, as is clearly evident from FIG. 6. Each of the three tightening straps 14, 15, and 16 has its end 17, 18, and 19 brought to the appropriate tightening strap between the rings 11, 12, 13 and 8, 9, 10 (see FIG. 5) and attached in this region to the relevant tightening strap, while the free end of each of the tightening straps, in the form of the widenings 20, 21, and 22, is placed on the back of the relevant tightening strap in the direction of the opposite ring 11, 12, and 13. In this way, the wrist orthosis 1 is securely fastened to the appropriate wrist. As can be seen in FIG. 6, the opposite outer edges of the cuff are spaced apart from each other on an upper side 2U of the person's wrist, and the orthosis 1 is secured around the person's wrist by the tightening straps 14, 15, and 16 which extend between the rings (eyelets) on the opposite outer edges of the cuff.

What is claimed is:

1. A wrist orthosis including a cuff, the cuff comprising:
   a first thumb opening adapted for passage of a right thumb when the orthosis is on a person's right hand,
   a second thumb opening adapted for passage of the left thumb when the orthosis is on a person's left hand;
   at least one tensioning band for fixing the orthosis on the wrist,
   a central stabilizing rod extending between said first and second thumb openings, a first lateral stabilizing rod extending on an outer side of said first thumb opening, and a second lateral stabilizing rod extending on an outer side of said second thumb opening;
   wherein the first thumb opening is disposed between said central stabilizing rod and said first lateral stabilizing rod, the second thumb opening is disposed between said central stabilizing rod and said second lateral stabilizing rod, and
   each of said central stabilizing rod and said lateral stabilizing rods exhibiting a three-dimensional curvature in a region extending next to and along said thumb openings, wherein the three-dimensional curvature of the central stabilizing rod including a narrowed width portion and a relative long spoon-shape portion having a concave-shaped lower side facing away from a palm of the left or right hand of the person wearing the orthosis.

2. The wrist orthosis of claim 1, wherein said at least one tensioning band is guided through eyelets provided on opposite outer edges of said cuff and includes hook-and-loop fasteners allowing one end thereof to be attached to the tensioning band between said eyelets, and the other end thereof to be attached to a back of said tensioning band.

3. The wrist orthosis of claim 2, wherein ends of said at least one tensioning band are wider than the eyelets acting as barbed hooks to prevent any accidental slipping of the at least one tensioning band through said eyelets.

4. The wrist orthosis of claim 3, wherein said at least one tensioning band and at least one of said stabilizing rods are provided with openings.

5. The wrist orthosis of claim 2, wherein said at least one tensioning band and at least one of said stabilizing rods are provided with openings.

6. The wrist orthosis of claim 1, wherein said at least one tensioning band and at least one of said stabilizing rods are provided with openings.

7. The wrist orthosis of claim 1, wherein said central stabilizing rod is a single member having a narrow portion between the first and second thumb holes.

8. The wrist orthosis of claim 1, wherein said at least one tensioning band is guided through eyelets provided on opposite outer edges of said cuff and includes hook-and-loop fasteners allowing one end thereof to be attached to the tensioning band between said eyelets, and the other end thereof to be attached to a back of said tensioning band,
wherein the opposite outer edges of the cuff are spaced apart from each other on an upper side of the person's wrist, when the orthosis is secured around the person's wrist by the at least one tensioning band which extends between the eyelets on the opposite outer edges of said cuff.

* * * * *